United States Patent [19]

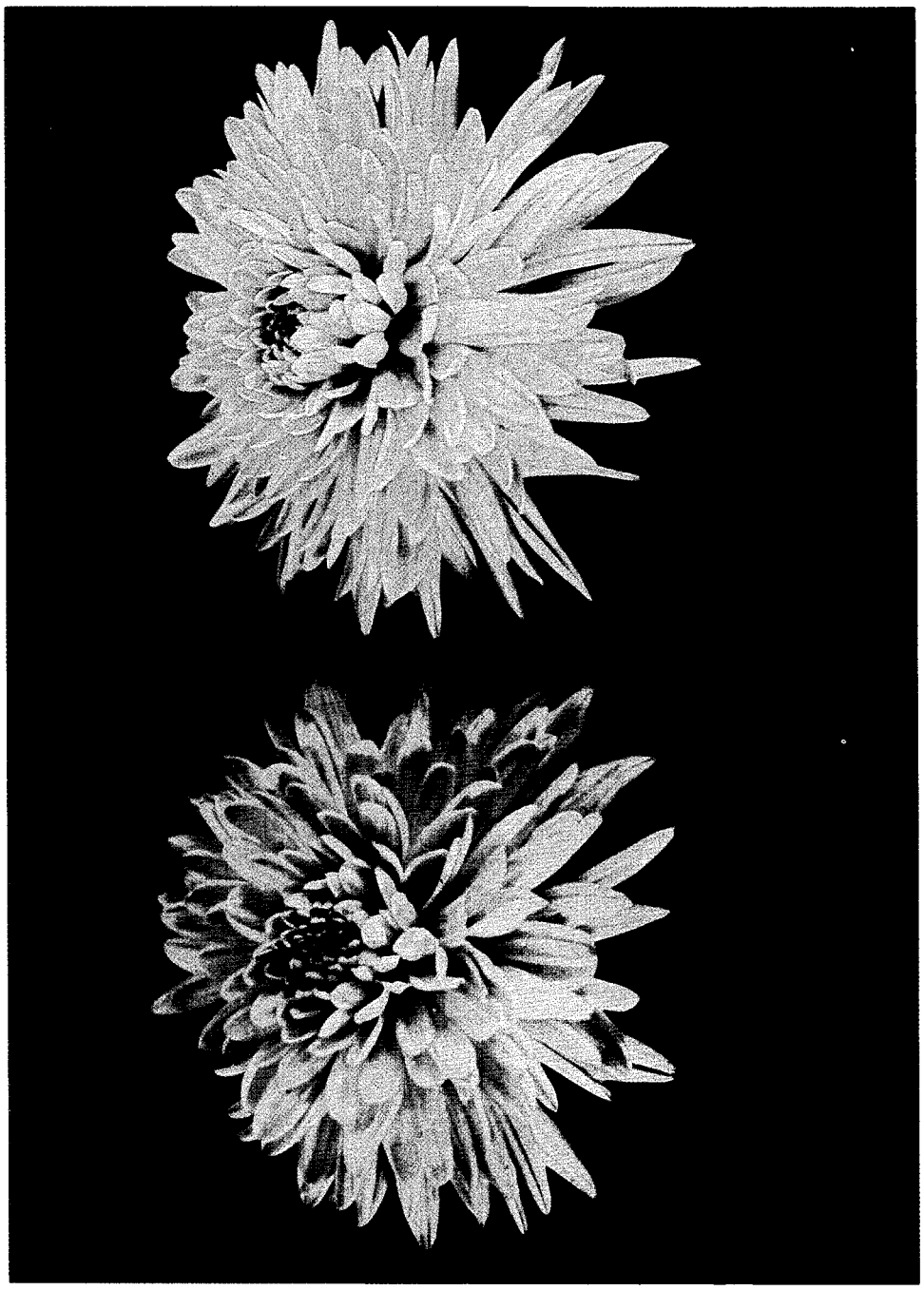

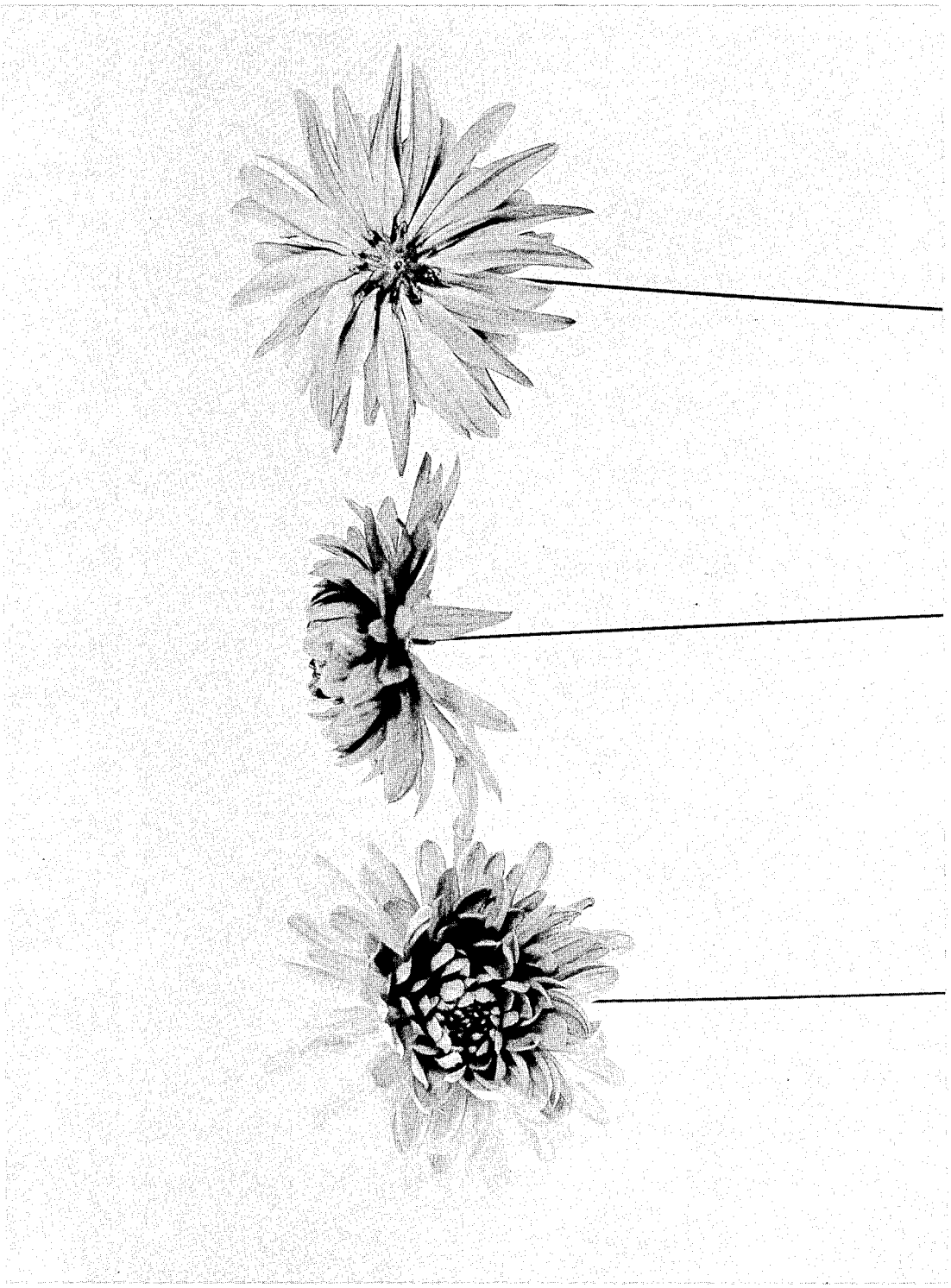

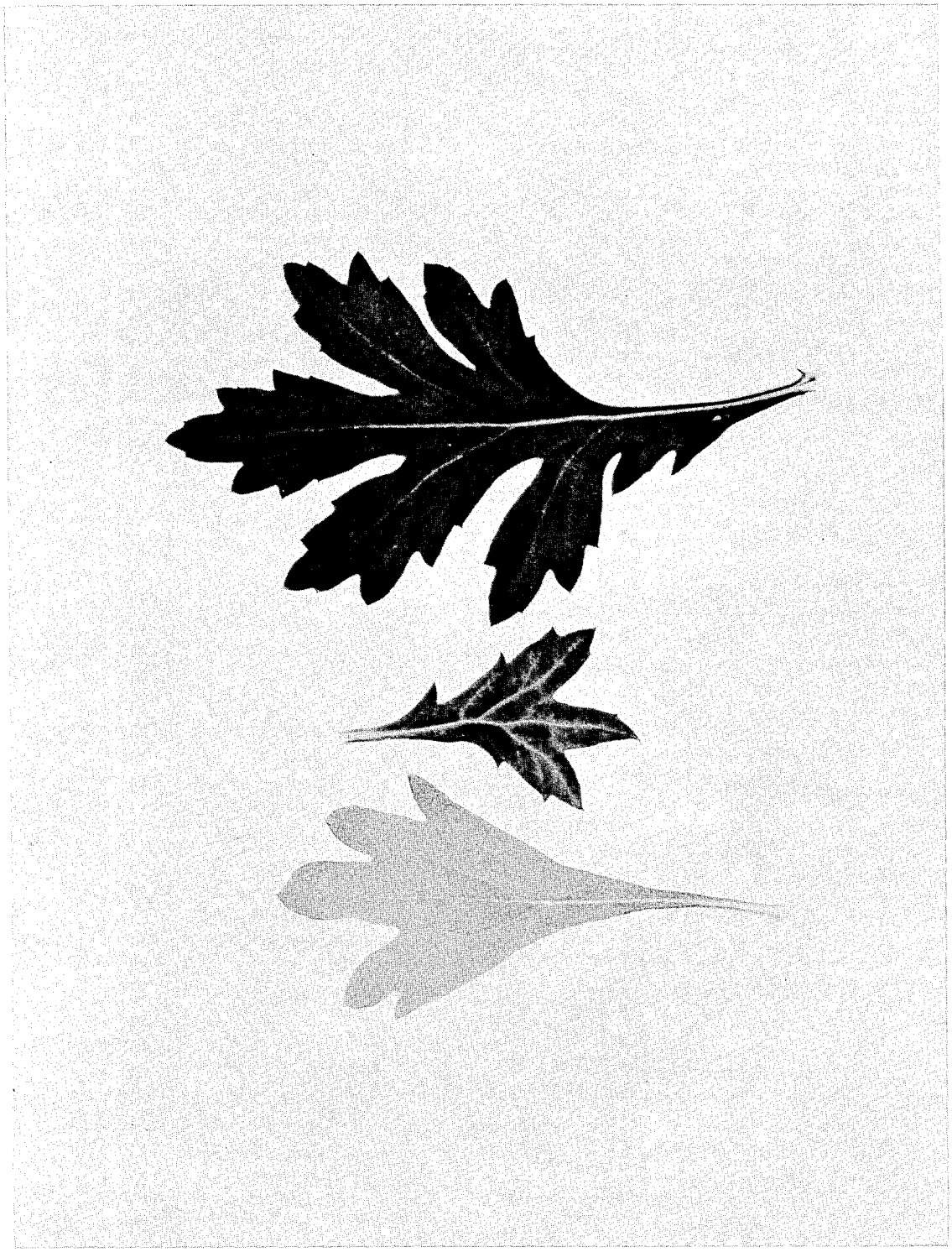

Niklas et al.

[11] Plant 4,087

[45] Aug. 2, 1977

[54] CHRYSANTHEMUM PLANT

[75] Inventors: Edmund R. Niklas, Clackamas, Oreg.; Jack M. Meek, Barberton; William E. Duffett, Akron, both of Ohio

[73] Assignee: Edmund R. Niklas, Clackamas, Oreg.

[21] Appl. No.: 677,411

[22] Filed: Apr. 15, 1976

[51] Int. Cl.[2] ..... A01H 5/00

[52] U.S. Cl. ..... Plt./76

[58] Field of Search ..... Plt./76, 81

*Primary Examiner*—Robert E. Bagwill

*Attorney, Agent, or Firm*—Donald D. Jeffery

EXEMPLARY CLAIM

1. A new and distinct cultivar of chrysanthemum plant known by the cultivar name Pinktive and particularly characterized as to uniqueness by the combined characteristics of decorative inflorescence type and semi-incurve inflorescence form; purple inflorescence color with uniform color oxidation; diameter across face of inflorescence up to 4 inches at maturity; uniform 9 week flowering response to photoperiodic short-day control; tall plant height; semi-spreading branching pattern, and dark green foliage with deeply lobed shape and coarsely serrated margin.

3 Drawing Figures

The present invention comprises a new and distinct cultivar of *Chrysanthemum morifolium,* Ramat., hereinafter referred to by the cultivar name Pinktive (No. 66145B05).

Pinktive is a spontaneous sport of Distinctive (No. 66145005, U.S. Plant Pat. No. 3,333). Pinktive was discovered and selected by Edmund R. Niklas in 1973 as one plant within a flowering block of Distinctive in a controlled environment in Clackamas, Ore.

The first act of asexual reproduction of Pinktive was accomplished when vegetative cuttings were taken from the initial Ohio by a technician working under formulations established and supervised by William E. Duffett and Jack M. Meek. Horticultural examination of selected units initiated July 25, 1974 has demonstrated that the combination of characteristics as herein disclosed for Pinktive are firmly fixed and are retained through successive generations of asexual reproduction.

Pinktive has not been observed under all possible environmental conditions. The phenotype may vary significantly with variations in environment such as temperature, light intensity, and day-length. The following observations, measurements, and comparisons describe plants grown in Barberton, Ohio under greenhouse environmental conditions which approximate those generally used in commercial practice, as described in Chart A which appears at the end of this specification. A light intensity chart of general use is shown in ASHAE Trans., Vol. 64, page 64, and reference is made thereto.

The following traits have been repeatedly observed and are determined to be basic characteristics of Pinktive which in combination distinguish this chrysanthemum as a new and distinct cultivar:

1. Decorative inflorescence type.
2. Semi-incurve inflorescence form.
3. Purple inflorescence color with uniform color oxidation.
4. Diameter across face of inflorescence up to 4 inches at maturity.
5. Uniform 9 week flowering response to photoperiodic short-day control.
6. Tall plant height (requiring 1–2 long day weeks prior to short days and 1–2 applications of 2500 ppm B9-SP to attain a flowered plant height from 14 to 18 inches).
7. Semi-spreading branching pattern.
8. Dark green foliage with deeply lobed shape and coarsely serrated margin.

The accompanying photographic drawings show typical inflorescence and foliage characteristics of Pinktive. It is noted that difficulty was encountered in obtaining photographs accurately representing the true inflorescence color of Pinktive. The color readings in the following description are, however, correct. Sheet 1 depicts the distinguishing feature of purple inflorescence color of Pinktive, which appears on the left, in comparision to the lavender pink inflorescence color of the parental cultivar Distinctive, which appears on the right. Sheet 2 is a black and white photograph showing three views of the inflorescence of Pinktive. Sheet 3 is a black and white photograph showing the foliage of Pinktive at three stages of growth.

Of the many commercial cultivars known to the present inventors, the most similar existing cultivar in comparison to Pinktive is the parental cultivar, Distinctive. Reference is made to attached Chart B which compares certain characteristics of Distinctive and Pinktive. It will be noted that Pinktive has different inflorescence color and different inflorescence form than the parental cultivar. The diameter across face of inflorescence, plant height, branching pattern, flowering response period, and inflorescence type of Pinktive are similar to those of Distinctive.

In the following description, color references are made to The Munsell Limit Color Cascade, 1972 edition. The color values were determined between 1:30 and 2:00 P.M. on February 10, 1976 under 150 foot-candle light intensity at Barberton, Ohio.

Botanical classification: *Chrysanthemum morifolium,* Ramat., cv Pinktive.

INFLORESCENCE

Capitulum:

*Form.*—Semi-incurved.

*Type.*—Decorative.
*Permanence.*—14–18 days.
*Diameter across.*—3.0 to 4.0 inches.

Corolla of ray florets:
*Texture (adaxial).*—Glabrous.
*Persistence.*—Resists shatter.
*Color (abaxial).*—46-6 to 44-5.
*Color (adaxial).*—46-3 to 44-3.

Reproductive organs:
*Androecium.*—Present disc florets only; scant pollen.
*Gynoecium.*—Present both ray and disc florets.

PLANT

General appearance: Semi-spreading; tall height.
Duration and texture: Perennial; herbaceous.
Foliage:
*Color (abaxial).*—Approximately 21-13 to 21-15 overlaid with grey.
*Color (adaxial).*—Approximately 21-13 overlaid with grey.
*Shape.*—Spatulate; deeply lobed.
*Texture.*—Glabrous.
*Venation.*—Prominent.
*Margin.*—Coarsely serrated.

We claim:

1. A new and distinct cultivar of chrysanthemum plant known by the cultivar name Pinktive and particularly characterized as to uniqueness by the combined characteristics of decorative inflorescence type and semi-incurve inflorescence form; purple inflorescence color with uniform color oxidation; diameter across face of inflorescence up to 4 inches at maturity; uniform 9 week flowering response to photoperiodic short-day control; tall plant height; semi-spreading branching pattern, and dark green foliage with deeply lobed shape and coarsely serrated margin.

* * * * *

CHART A
AVERAGE GREENHOUSE CHRYSANTHEMUM ENVIRONMENTS
USED FOR BARBERTON, OHIO

| SEASON | TEMPERATURES USED Night | Bright Day | Cloudy Day | LIGHTING USED | BLACK CLOTH USED | SUPP $CO_2$ |
|---|---|---|---|---|---|---|
| FALL | 65° F to | 65° F to | 60° F to | 2 to 4 weeks at 3 Hours Per Night | To Sept. 15 on - 5:30 PM | From Oct. 15 |
| | 56° F | 80° F | 75° F | of 7–10 f.c. | Off - 7:30 AM | 300 ppm |
| WINTER | 58° F to | 65° F to | 60° F to | 2 to 5 weeks at 5 hours Per Night | NONE | 300 ppm |
| | 62° F | 70° F | 65° F | of 7–10 f.c. | | |
| SPRING | 58° F to | 65° F to | 60° F to | 2 to 4 weeks at 5 Hours Per Night | From Mar. 15 on - 5:30 PM | To Apr. 15 |
| | 65° F | 80° F | 75° F | of 7–10 f.c. | Off - 7:30 AM | 300 ppm |
| SUMMER | 62° F to | 70° F to | 65° F to | 1 to 2 weeks at 3 Hours Per Night | on - 6:00 PM | NONE |
| | 68° F | 90° F | 75° F | of 7–10 f.c. | Off - 8:00 AM | |

CHART B
COMPARISON OF PINKTIVE AND DISTINCTIVE

| CULTIVAR | INFLORESCENCE COLOR | DIAMETER ACROSS FACE OF INFLORESCENCE | PLANT HEIGHT | BRANCHING PATTERN | FLOWERING RESPONSE PERIOD | INFLORESCENCE FORM AND TYPE |
|---|---|---|---|---|---|---|
| Pinktive | Purple | 3.0 to 4.0 inches | Tall | Semi-spreading | 9 week | Semi-incurved decorative |
| Distinctive | Lavender pink | 3.0 to 4.0 inches | Tall | Semi-spreading | 9 week | Flat semi-cactus decorative |

COMPARISONS MADE OF PLANTS GROWN IN A GREENHOUSE IN BARBERTON, OHIO UNDER ENVIRONMENTAL CONDITIONS AS DESCRIBED IN CHART A

UNITED STATES PATENT AND TRADEMARK OFFICE

CERTIFICATE OF CORRECTION

PATENT NO. : PP-4087

DATED : August 2, 1977

INVENTOR(S) : EDMUND R. NIKLAS, JACK M. MEEK and WILLIAM E. DUFFETT

It is certified that error appears in the above-identified patent and that said Letters Patent are hereby corrected as shown below:

In Column 1, line 12, after "initial" and before "Ohio" the following should be inserted --selection in August, 1973 in a controlled environment, in Barberton,--.

Signed and Sealed this

*Eighteenth* Day of *April 1978*

[SEAL]

*Attest:*

RUTH C. MASON
*Attesting Officer*

LUTRELLE F. PARKER
*Acting Commissioner of Patents and Trademarks*